United States Patent [19]
Merrick et al.

[11] Patent Number: 6,043,267
[45] Date of Patent: Mar. 28, 2000

[54] FUNGICIDAL COMPOSITIONS AND THE USE THEREOF

[75] Inventors: James Edward Merrick, Perrysville, Ohio; Thomas Edward Vrabel, Raleigh, N.C.

[73] Assignee: Rhone-Poulenc Agrochimie, Lyons, France

[21] Appl. No.: 08/981,213

[22] PCT Filed: Jun. 12, 1996

[86] PCT No.: PCT/EP96/02542

§ 371 Date: May 1, 1998

§ 102(e) Date: May 1, 1998

[87] PCT Pub. No.: WO97/00013

PCT Pub. Date: Jan. 3, 1997

Related U.S. Application Data

[60] Provisional application No. 60/000,330, Jun. 19, 1995.

[51] Int. Cl.$^7$ .................................................. A01N 43/80
[52] U.S. Cl. .............................................................. 514/378
[58] Field of Search ............................................... 514/378

[56] References Cited

U.S. PATENT DOCUMENTS

| | | | |
|---|---|---|---|
| 3,629,430 | 12/1971 | Yukiyoshi et al. | 424/272 |
| 5,656,573 | 8/1997 | Roberts et al. | 504/271 |

FOREIGN PATENT DOCUMENTS

| | | |
|---|---|---|
| 0418175 | 3/1991 | European Pat. Off. |
| 0487357 | 5/1992 | European Pat. Off. |
| 0527036 | 2/1993 | European Pat. Off. |
| 0560482 | 9/1993 | European Pat. Off. |
| 94/18179 | 8/1994 | WIPO . |
| 95/22904 | 8/1995 | WIPO . |

OTHER PUBLICATIONS ianrwww.unl.edu/pubs/plantdisease/g742.htm (Watkins et al, "Dollar Spot Disease of Turfgrass", G85–742–A, Revised May 1990, University of Nebraska, Lincoln, Nebraska).

www.ag.ohio–state.edu/~ohioline/hyg–fact/3000/3075.html (Rimelspach et al, "Dollar Spot on Turfgrass", HYG–3075–96,Ohio State University, Columbus, Ohio, 1996).

Balance® WDG Herbicide, label, Rhône–Poulenc Ag Company, Research Triangle Park, North Carolina, 1999.

*Primary Examiner*—Allen J. Robinson
*Attorney, Agent, or Firm*—Burns, Doane, Swecker & Mathis, L.L.P.

[57] ABSTRACT

The invention relates to a method for the control of fungi at a locus which comprises applying to the locus a fungicidally effective amount of an isoxazole derivative of formula (I), wherein R is hydrogen or —$CO_2R^3$, wherein $R^3$ is as defined below, $R^1$ is cyclopropyl; $R^2$ is selected from halogen, —$S(O)_pR^4$ and $C_{1-4}$alkyl or haloalkyl; n is two or three; p is zero, one or two; $R^3$ is $C_{1-4}$alkyl and $R^4$ is $C_{1-4}$alkyl; and to compositions containing the same.

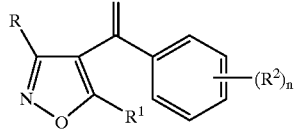

(I)

32 Claims, No Drawings

FUNGICIDAL COMPOSITIONS AND THE USE THEREOF

This application is the U.S. national stage of International Application No. PCT/EP96/02542, filed Jun. 12, 1996 and designating the United States, which claims the priority of U.S. Provisional Patent Application No. 60/000,330, filed Jun. 19, 1995, now abandoned.

BACKGROUND OF THE INVENTION

I Field of the Invention

This invention relates to a new method of controlling fungi and weeds, and in particular it relates to a new method of protecting turf against both fungicidal diseases and weeds infestation.

II Discussion of the Prior Art

Protection of turf has always been a difficult problem because the users of turfs are generally very demanding people who require a top quality of the turf. The severe requirements are probably due to their aesthetic needs which are far away of the classical requirements of agricultural users such as farmers, who needs are directed to production considerations which do not involve anything on the appearance of the fields.

The difficulty of protecting turf is that there are generally and simultaneously both weeds infestations and fungicidal attacks which require both herbicidal and fungicidal treatments. The problem is thus made more difficult because, generally, the herbicidal compounds are not fungicidal and the fungicidal compounds are not herbicidal. Further it is generally necessary to strongly limit the number of treatment of turf because numerous passages of treatment machines may damage the turf so that this creates a third source of problem and increase the risks of impairing the said turf to an unacceptable level.

A further problem of turf care is the control of dollar spot disease (the causal agent for this disease being *Sclerotinia homeocarpa*). No single fungicidal compound is able to completely control this disease which is quite specific.

A still further problem of turf care is that the pesticidal treatment should be safe and not phytotoxic for the desired turfgrass, especially for one or more of the following grasses: *Agrostis stolinifera, Festuca arundinacea, Festuca rubra, Lolium perenne, Poa pratensis* and *Poa annua*.

Treatment of crops against weed infestation by isoxazoles is known, for example from European Patent Publication Nos. 0418175, 0487357, 0527036 and 0560482. However, no indication is known that these publications that isoxazoles could meet the above cited requirements with regard to the control of turf weeds. Furthermore, there is no indication that the isoxazoles possess any fungicidal properties.

An object of the invention is therefore to provide a method of protecting turf against fungicidal diseases.

A further object of the invention is to provide a method of protecting turf which is susceptible to be infested or contaminated by dollar spot disease.

A still further object of the invention is to provide a method of control of dollar spot disease on turf.

A still further object of the invention is to provide a method of control of dollar spot disease on turf which is safe for one or more of the grass species selected from the group comprising *Festuca arundinacea, Festuca rubra, Lolium perenne, Poa pratensis* and *Poa annua*.

A still further object of the invention is to provide a method of simultaneously controlling weeds and fungal infections found in turf.

A still further object of the invention is to overcome the existing problem of turf care, especially the problems as here above explained.

Surprisingly it has been found that these problems may be overcome in whole or in part by the method of the invention.

SUMMARY OF INVENTION

In one aspect the invention provides a method for the control of fungi at a locus which comprises applying to the locus an effective amount of an isoxazole derivative of formula I:

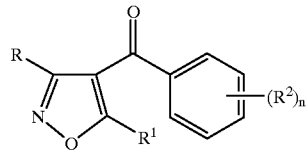

wherein
R is hydrogen or $-CO_2R^3$, wherein $R^3$ is as defined below;
$R^1$ is cyclopropyl;
$R^2$ is selected from halogen, $-S(O)_pR^4$, $C_{1-4}$ alkyl or $C_{1-4}$ haloalkyl;
n is two or three; p is zero, one or two;
$R^3$ is $C_{1-4}$ alkyl and
$R^4$ is $C_{1-4}$ alkyl.

DETAILED DESCRIPTION OF THE INVENTION

According to a specific aspect of the invention, the isoxazole is a herbicidally active isoxazole derivative.

Preferably R represents hydrogen.

Compounds of formula I above in which the groups $(R^2)_n$ are in the 2,4- or 2,3,4-positions of the benzoyl ring are also preferred.

Preferably $R^2$ is selected from the group consisting of halogen, $-S(O)_pR^4$ and $-CF_3$.

Preferably one of the groups $R^2$ represents $-S(O)_pR^4$, wherein $R^4$ is methyl.

The preferred compound of the invention is 5-cyclopropyl-4-(2-methylsulphonyl-4-trifluoromethyl) benzoylisozaxole, hereafter referred to as Compound 1.

In the method of the invention the locus is preferably an area comprising turfgrasses, in particular one or more of *Festuca arundinacea, Festuca rubra, Lolium perenne, Poa pratensis* and *Poa annua*.

The fungi controlled by the method of the invention is preferably dollar spot disease (*Sclerotinia homeocarpa*), which as mentioned above, is a particular problem of turfgrasses.

The method of the invention is preferably used under preventative conditions, i.e. when fungal infection of the locus is about to occur. It is also preferred to apply the isoxazole derivative of formula (I) above to established turfgrass areas.

The effective amount of isoxazole derivative which is used in the invention is generally from 80 to 300 g/ha, preferably from 100 to 230 g/ha.

Unless otherwise specified, the percentage cited in the instant specification are by weight.

The treatment of turf according to the invention is advantageously made by spraying a solid or liquid composition comprising the said isoxazole derivative.

The compositions which may be used in the invention for the fungicidal treatment of the invention are similar to the known herbicidally active compositions comprising an isoxazole derivative.

These compositions may comprise from 0.001 to 95% of the isoxazole derivative.

The liquid diluted formulations as applied to the turf comprise generally from 0.001 to 3% of isoxazole derivative, preferably from 0.1 to 0.5%.

The solid formulations as applied to the turf comprise generally from 0.1 to 8% of isoxazole derivative, preferably from 0.5 to 1.5%.

The concentrated compositions are the compositions which are commercialized or transported or stored. For application to plant they are normally diluted in water and applied in such a diluted form. The diluted form is part of the invention as well as the concentrated forms.

The concentrated formulations comprise generally from 5 to 95% of isoxazole derivative, preferably from 10 to 50%.

The compositions of the invention may be applied once, or more than once, or throughout the whole fungi season. Usually fungicidal compositions according to the invention are applied to the turf area at a rate of from 0.04 to 2 kg/ha of active ingredient, preferably from 0.1 to 1 kg/ha.

The fungicidal concentrated compositions according to the invention may be in the form of a solid, e.g. dusts or granules or wettable powders, or, preferably, in the form of a liquid, such as an emulsifiable concentrate or a true solution.

The fungicidal compositions according to the instant invention generally comprise from 0.5 to 95% of active ingredient. The remaining part up to 100% comprises a carrier as well as various additives such as those here after indicated.

By "carrier", it is herein meant an organic or inorganic material, which may be natural of artificial or synthetic, and which is associated to the active ingredients and which facilitates its application to the turf. This carrier is thus generally inert and should be agriculturally acceptable, especially on the contemplated or treated turf. The carrier may be solid (clay, silicates, silica, resins, wax, fertilizers, etc.) or liquid (water, alcohols, ketones, oil solvent, saturated or unsaturated hydrocarbons, chlorinated hydrocarbons, liquefied gas, etc.).

Among the many additives, the compositions of the invention may comprise surfactants as well as dispersants or stickers or antifoam agent or antifreezing agents or dyestuffs or thickeners, or adhesives or protecting colloids, penetrating agents, stabilizing agents, sequestering agents, antiflocculating agents, corrosion inhibitors, pigments, polymers.

More generally the compositions of the invention may comprise all kind of solid or liquid additives which are known in the art of fungicides and fungicidal treatments.

The surfactant may be emulsifying or wetting, ionic or non ionic. Possible surfactants are salts of polyacrylic or lignosulfonic acids, salts of phenolsulfonic or naphtalenesulfonic acids; polycondensates of ethylene oxide with fatty alcohols or fatty acids or fatty amines or substituted phenols (particularly alkylphenols or arylphenols); esters-salts of sulfosuccinic acids, taurine derivatives, such as alkyl taurates; Phosphoric esters of alcohols or polyoxyethylated phenols. The use of at least one surfactant is generally required because the active ingredients are not water soluble while the spraying vehicle is water.

The method of application of the compositions of the invention is generally the spraying of a mixture which has been previously made by dilution of more concentrated formulations according to the invention.

Solid compositions may powders for dusting or for dispersion and granule, especially extruded or compacted granules, or granules which have been made by impregnation of a powder (the content of active ingredients present in such powders will generally be from 1 to 80%).

Liquid compositions or compositions which have to be liquid when applied include solutions, water soluble concentrates emulsifiable concentrates, emulsions, wettable powders or pastes, water dispersible granules.

Emulsifiable concentrates comprise generally 10 to 80% of active ingredient; the emulsions when applied comprise generally 0.01 to 20% of active ingredient.

For example, the emulsifiable concentrates may comprise the solvent and further, as far as needed, 2 to 20% of suitable additives as stabilizers, surfactants, penetrating agents, corrosion inhibitors, or other additives already recited.

These concentrates are usually diluted in tank water so as to obtain the dilution appropriate for spraying.

The concentrated suspensions may also be applied by spraying and should be fluid without letting any solid to separate and falling at the bottom. Generally they comprise 1 to 75% of active ingredients (preferably 2 to 50%), 0.5 to 15% of surfactants, 0.1 to 10% of thickeners, 0 to 10% of other suitable additives as already indicated, and further water or an organic liquid wherein the active ingredient is insoluble or has a low solubility.

The wettable powders generally comprise the active ingredients (1 to 95%, preferably 2 to 80%), the solid carrier, a wetting agent (0 to 5%), a dispersing agent (3 to 10%) and, as far as needed, 0 to 10% of other additives such as stabilizers and other as already listed In order to obtain these wettable powders or dusting powders, it is appropriate to intimately mix the active ingredients and the additives, to grind in a mill or similar devices.

Dispersible granules are generally made by agglomeration of a powder followed by an appropriate granulation process.

The emulsions herein described may be of type oil-in water or water-in-oil. They may more or less thick up to be like gels.

It will be understood that the composition or formulation used will vary depending to specific conditions of the treatment problem.

The compositions of the inventions may also be used in admixtures with another pesticide e.g. an insecticide, acaricide or herbicide.

The following are examples of representative compositions of the invention. In the description that follows the following are trade marks: REAX, Sellogen, Barden, Aerosil, Igepal, Rhodafac, Biodac.

EXAMPLE C1

The following composition was prepared as a wettable dispersible granule (the percentages that follow are by weight):

| | |
|---|---|
| Isoxazole derivative (Compound 1): | 75.0% |
| REAX 88A (Surfactant): | 10.0% |
| Sellogen HR (Surfactant): | 3.0% |
| Barden AG-1 (Clay): | 11.0% |
| Aerosil R972 (Silica filler) | 1.0% |

EXAMPLE C2

The following composition was prepared as a granule (the percentages that follow are by weight):

| | |
|---|---|
| Isoxazole derivative (Compound 1): | 0.38% |
| Igepal CA630 (surfactant): | 1.0% |
| Rhodafac RE610 (surfactant): | 1.0% |
| N-methylpyrollidine (solvent) | 7.0% |
| Biodac (20/40) (synthetic granule) | 90.62% |

The isoxazole derivatives used in the method of the invention are known from European Patent Publication Nos. 0418175, 0487357, 0527036 and 0560482, or can be prepared according to the methods described in these documents.

The invention is illustrated by the following examples which are not considered as limiting the invention but are given to better enable the skilled worker to use it.

EXAMPLE A1

The composition described in Example C1 above (100 g) was diluted in water (100 liters) and was sprayed on a 10 square meter turf stand in the Spring season. The application conditions were such that a dose rate equivalent to 202 grammes of Compound 1 per hectare was used, which corresponds to a concentration of Compound 1 of 390 ppm (parts per million).

The turf stand comprised a mixed population of creeping bentgrass (*Agrostis stolinifera*) and annual bluegrass (*Poa annua*). The stand was managed as a turf green and was mowed to a height of 4.75 mm. Contamination of this turf stand by dollar spot disease was from natural infection.

The results were noted by mean of the visual estimation of the number of fungi spots per square meter and transformed in a percentage of action by comparison with a similar untreated turf area. A 0% notation means that the treated turf was in the same conditions as the untreated standard. A 100% notation means that the treated turf was totally free of fungi disease.

91 days after treating the turf stand with the composition, an efficacy of 77.1% was observed.

103 days after treating the turf stand with the composition, an efficacy of 88.4% was observed.

EXAMPLE 2

Example 1 was repeated, except that the application conditions were such that a dose rate equivalent to 403 grammes of Compound per hectare was used, which corresponds to a concentration of Compound 1 of 780 ppm.

91 days after treating the turf stand with the composition, an efficacy of 93.3% was observed.

103 days after treating the turf stand with the composition, an efficacy of 95.2% was observed.

EXAMPLE 3

An in vitro study was set up to determine the ability of the compounds of the invention to inhibit the graph of *Sclerotinia homoecarpa*, the causal agent of dollar. A stock solution of Compound 1 technical material) in acetone was prepared. Potato dextrose agar (PDA) plates augmented with 10, 100 and 1000 ppm of Compound 1 were then made. Two sets of control plates were used; one contained corresponding amounts of acetone and the other contained PDA only. Four replicates were performed. An 8 mm diameter plug of fungal mycelia (*Sclerotinia homoecarpa*) was placed in the center of each plate, which were then incubated at room temperature for four days. As the growth of fungi on the untreated control reached the edge of the plates, the diameter of growth of the acetone control and the plates treated with Compound 1 were determined. The figures in the Table below represent the diameter of growth of the plug (Rep. means replicate number).

RESULTS

| Rep. | PDA only | Acetone Control (ppm) | | | Compound 1 (ppm) | | |
|---|---|---|---|---|---|---|---|
| | | 10 | 100 | 1000 | 10 | 100 | 1000 |
| 1 | 80 | 80 | 80 | 26 | 0 | 1 | 0 |
| 2 | 80 | 80 | 80 | 0 | 3 | 2 | 0 |
| 3 | 80 | 80 | 80 | 14 | 5 | 1 | 0 |
| 4 | 80 | 80 | 80 | 25 | 1 | 2 | 0 |

What is claimed is:

1. A method for the control of fungi comprising applying to said fungi or to a locus attacked by said fungi a fungicidally effective amount of a compound of the formula (I):

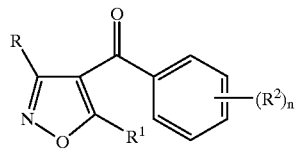

(I)

wherein:

R is hydrogen or $—CO_2R^3$;

$R^1$ is cyclopropyl;

$R^2$ is halogen, $—S(O)_pR^4$, $C_{1-4}$ alkyl or haloalkyl;

n is two or three;

p is zero, one or two;

$R^3$ is $C_{1-4}$ alkyl; and $R^4$ is $C_{1-4}$ alkyl.

2. A method according to claim 1, wherein $R^2$ is halogen, $—S(O)_pR^4$ or $—CF_3$.

3. A method according to claim 1, wherein one of the groups $R^2$ is $—S(O)_pR^4$ wherein $R^4$ is methyl.

4. A method according to claim 1, wherein the compound of formula (I) is 5-cyclopropyl-4-(2-methylsulphonyl-4-trifluoromethyl)benzoylisoxazole.

5. A method according to claim 1, wherein said locus is an area comprising a turfgrass.

6. A method according to claim 5, wherein the turfgrass comprises *Festuca arundinacea, Festuca ruba, Lolium perenne, Poa pratensis* or *Poa annua*.

7. A method according to claim 1, wherein the fungi cause dollar spot disease.

8. A method according to claim 7, wherein the fungi are *Sclerotinia homeocarpa*.

9. A method according to claim 1, wherein from 80 to 300 g of the compound of formula (I) are applied per hectare.

10. A method according to claim 9, wherein from 100 to 230 g of the compound of formula (I) are applied per hectare.

11. A method according to claim 2, wherein one of the groups $R^2$ is —$S(O)_pR^4$ wherein $R^4$ is methyl.

12. A method according to claim 2, wherein said locus is an area comprising a turfgrass.

13. A method according to claim 12, wherein the turfgrass comprises *Festuca arundinacea, Festuca ruba, Lolium perenne, Poa pratensis* or *Poa annua*.

14. A method according to claim 2, wherein the fungi cause dollar spot disease.

15. A method according to claim 2, wherein from 80 to 300 g of the compound of formula (I) are applied per hectare.

16. A method according to claim 15, wherein from 100 to 230 g of the compound of formula (I) are applied per hectare.

17. A method according to claim 3, wherein said locus is an area comprising a turfgrass.

18. A method according to claim 17, wherein the turfgrass comprises *Festuca arundinacea, Festuca ruba, Lolium perenne, Poa pratensis* or *Poa annua*.

19. A method according to claim 3, wherein the fungi cause dollar spot disease.

20. A method according to claim 3, wherein from 80 to 300 g of the compound of formula (I) are applied per hectare.

21. A method according to claim 20, wherein from 100 to 230 g of the compound of formula (I) are applied per hectare.

22. A method according to claim 4, wherein said locus is an area comprising a turfgrass.

23. A method according to claim 22, wherein the turfgrass comprises *Festuca arundinacea, Festuca ruba, Lolium perenne, Poa pratensis* or *Poa annua*.

24. A method according to claim 4, wherein the fungi cause dollar spot disease.

25. A method according to claim 4, wherein from 80 to 300 g of the compound of formula (I) are applied per hectare.

26. A method according to claim 25, wherein from 100 to 230 g of the compound of formula (I) are applied per hectare.

27. A method according to claim 5, wherein the fungi cause dollar spot disease.

28. A method according to claim 6, wherein the fungi cause dollar spot disease.

29. A method for the control of the fungi *Sclerotinia homeocarpa* in an established turfgrass, said method comprising applying to an established turfgrass, said turfgrass being attacked by or susceptible to attack by said fungi and comprising *Festuca arundinacea, Festuca ruba, Lolium perenne, Poa pratensis* or *Poa annua,* from 80 to 300 g of the compound 5-cyclopropyl-4-(2-methylsulphonyl-4-trifluoromethyl)benzoylisoxazole per hectare, under conditions in which said turfgrass is susceptible to said fungi.

30. A method according to claim 29, wherein from 100 to 230 g of 5-cyclopropyl-4-(2-methylsulphonyl-4-trifluoromethyl)benzoylisoxazole are applied per hectare.

31. A method according to claim 29, wherein 5-cyclopropyl-4-(2-methylsulphonyl-4-trifluoromethyl)benzoylisoxazole is applied under preventative conditions.

32. A method according to claim 30, wherein 5-cyclopropyl-4-(2-methylsulphonyl-4-trifluoromethyl)benzoylisoxazole is applied under preventative conditions.

* * * * *